United States Patent [19]

Rogalsky

[11] Patent Number: 5,084,393
[45] Date of Patent: Jan. 28, 1992

[54] CONTAINER FOR A BIOLOGICAL CULTURE

[76] Inventor: Alena Rogalsky, 186 Pinehurst Ave., New York, N.Y. 11746

[21] Appl. No.: 459,724

[22] PCT Filed: Aug. 28, 1989

[86] PCT No.: PCT/US89/03706

§ 371 Date: Aug. 28, 1989

§ 102(e) Date: Aug. 28, 1989

[51] Int. Cl.$^5$ .............................................. C12M 3/00
[52] U.S. Cl. ................................... 435/284; 435/296; 206/223; 215/1 C
[58] Field of Search ............... 435/284, 287, 296; 206/223; 215/1 C

[56] References Cited

U.S. PATENT DOCUMENTS

| | | | |
|---|---|---|---|
| 3,532,605 | 10/1970 | Riera | 435/296 |
| 3,853,712 | 12/1974 | House et al. | 435/296 |
| 3,941,661 | 3/1976 | Noteboom | 435/296 |
| 4,024,975 | 5/1977 | Uhlig | 215/1 C |
| 4,121,976 | 10/1978 | Gleeson | 435/296 X |
| 4,665,035 | 5/1977 | Tunac | 435/296 |
| 4,734,373 | 3/1988 | Bartal | 435/296 |
| 4,790,361 | 12/1988 | Jones et al. | 215/1 C |
| 4,824,787 | 4/1989 | Serkes | 435/285 |

Primary Examiner—Larry Jones
Attorney, Agent, or Firm—Ilya Zborovsky

[57] ABSTRACT

A container for biological culture (1, 1') has a wall which limits an inner chamber with an area (2) for growing cells. The wall has a brush-like wall portion (4, 8) with a plurality of bristle-shaped projections (5, 5') extending into the area (2) for growing cells. The container (1, 1') has a significantly increased area for growing cells.

18 Claims, 8 Drawing Sheets

CONTAINER FOR A BIOLOGICAL CULTURE

DESCRIPTION

1. Technical Field

My invention relates to containers for biological cultures for example for growing cells.

Containers for biological cultures are formed for example as flasks or roller bottles. They are to be filled with a nutrient medium, and cells are then grown in the containers. A known container of this type is as a rule a vessel of a round, rectangular or other cross-section with substantially smooth inner walls and bottom. The output of the container depends on a surface available for growing of cells.

2. Background Art

For increasing the area of cell growing it is known to introduce into the container additional surfaces, to form the container by a plurality of flat dishes which are stackable over one another, and produce additional formations in the container. In one of the known containers of this type disclosed in U.S. Pat. No. 4,824,787 a plurality of corrugations are provided, which increase the area of growing cells. The increase of the area achieved in this construction is however very limited, and it is to be understood that it is desired to increase further the area for growing cells and therefore to increase the output of the containers for biological cultures.

DISCLOSURE OF INVENTION

In accordance with the present invention, I provide a container for a biological culture, particularly for growing cells, which has a wall limiting an inner chamber with an area for growing cells in a solution, wherein the wall has at least one wall portion formed as a brush with a plurality of bristle-shaped projections extending into said area for supporting cells.

My improved container for biological culture possesses the advantage that the bristle-shaped projections provide a considerably increased surface for supporting cells than any other formations known in the art. Each bristle is connected with the wall only at its end, while the opposite end of the bristle as well as its side surface and surfaces at all sides are available for supporting the cells.

The brush-like wall portion can be a portion near which a solution is accumulated, so that the bristle-shaped projections extend from this wall portion and are completely covered with the solution. On the other hand the brush-like wall portion can be opposite to a wall portion near which a solution is accumulated, so that the bristle-shaped projections extend toward the wall at which the solution is accumulated. The bristle-shaped projections always have a height which is greater than their thickness, and can be rigid or flexible. They can have different shapes which are suitable for growing of cells on them.

In a container formed in accordance with the present invention as a roller bottle the cells grow not only in the area located in the region of the main body of nutrient solution. Since the projections are bristle shaped, they retain the nutrient solution even when they are withdrawn from its main body during rotation of the bottle. Thereby the cells also grow in the regions outside the main body of the solution on the projections on which the solution is retained and slowly flows down from them.

BRIEF DESCRIPTION OF DRAWINGS

The details of my invention will be described in connection with the accompanying drawings, in which FIGS. 33, 34 and 35 are side views

BEST MODE FOR CARRYING OUT THE INVENTION

Figure 1:
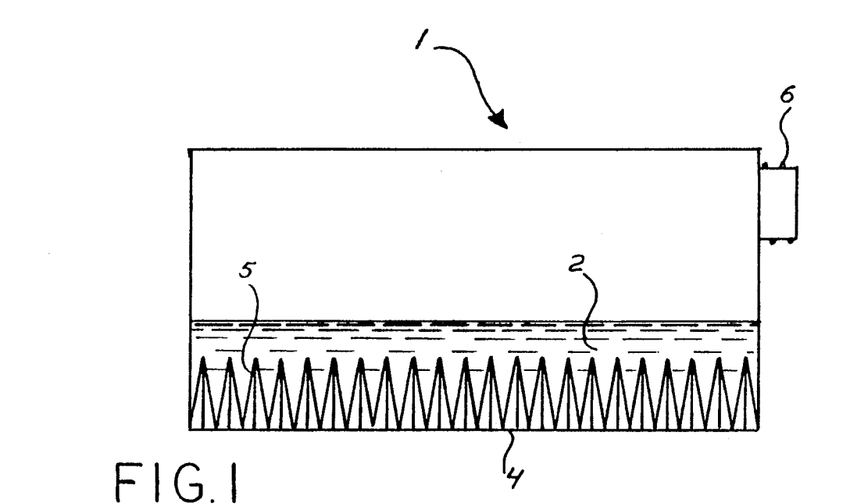
FIGS. 1, 2, 3 are a side view at transverse section and a partial view of a bottom of a container for biological culture formed as a flask.
Figure 2:
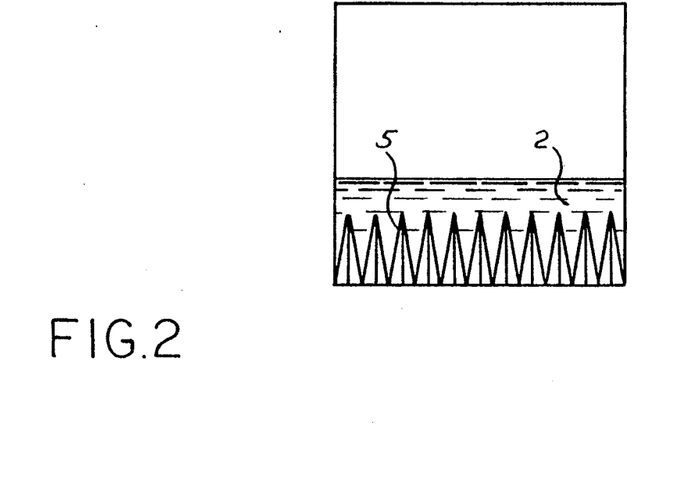
Figure 3:
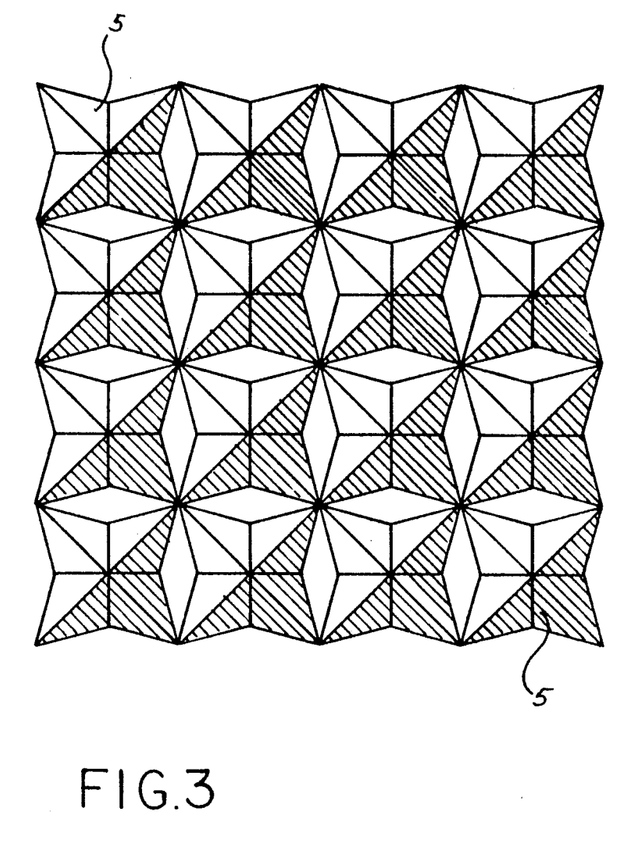

A container in accordance with one embodiment of the present invention, for biological culture for example for growing cells is shown in FIGS. 1–3. The container is identified as a whole with reference numeral 1 and has a wall which limits an inner chamber with an area 2 for accumulating a nutrient solution and growing cells. The container has a bottom 4 which is formed as a brush with a plurality of bristle-shaped projections 5. The container further has a top, two side walls, and two end walls. A neck 6 is formed in one of the side walls As can be seen from the drawings in the container in accordance with this embodiment, the brush-like wall is the bottom near which the nutrient solution is accumulated and the cells are to be grown. The container 1 can be made of glass, a synthetic plastic material, etc. as well known in the art. The projections 5 can be made of one piece with the bottom 4, and the bottom 4 with the projections can then be connected with the remaining part of the container. On the other hand, it is possible to make the container simultaneously with all the walls and the projections 5 on the bottom 4.

The height of the bristle-shaped projections 4 is greater than their thickness in accordance with an important feature of the present invention. It is advantageous when the height of the bristle-shaped projections is many times greater than their thickness, for example the bristle-shaped projections can have a thickness of several tenth microns while their height can be up to several centimeters. The area of the bristle-shaped projections is many times greater than the area of the smooth inner surface of the bottom, so that a significant increase of the useful area for growing cells is obtained.

As can be seen from FIG. 3, the bristle-shaped projections 5 have a polyhydral shape. In other words, each bristle-shaped projection has a plurality of side surfaces which considerably increase their area. This not only increases the area for growing cells, but also improves their retention of the individual bristle-shaped projections.

Figure 4:
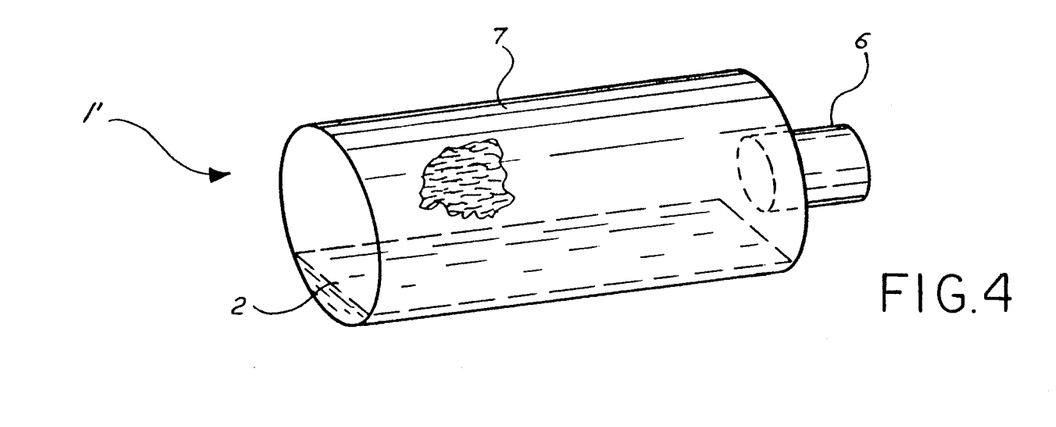
FIGS. 4, 5 and 6 are a side view, a section and a view of an inner surface of the container for biological culture formed as a roller bottle.
Figure 5:
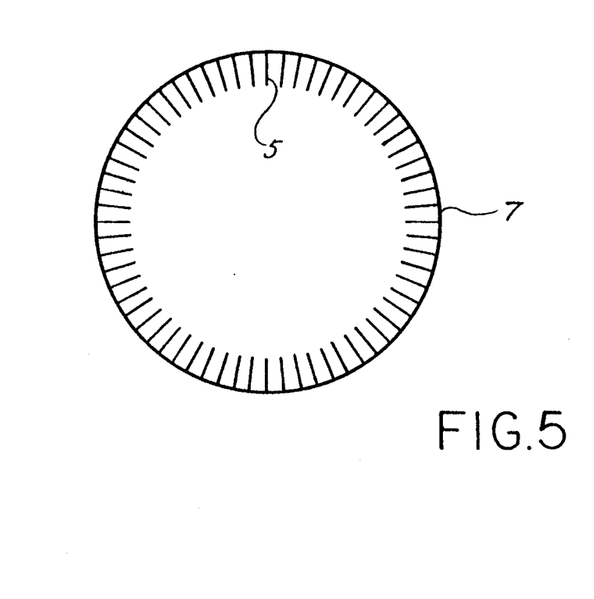
Figure 6:
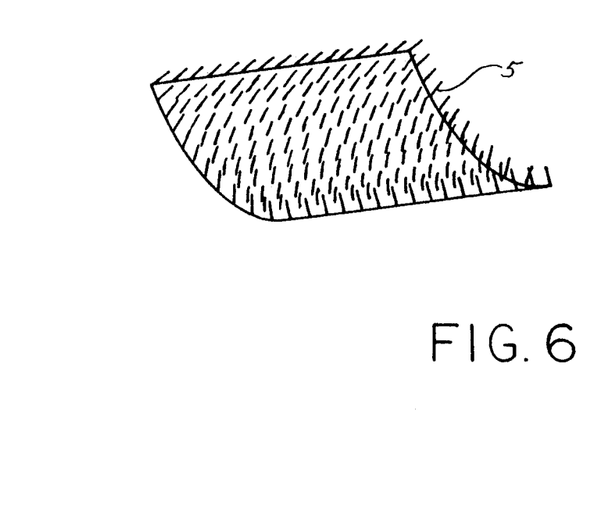

In the embodiment shown in FIGS. 4, 5 and 6 the container 1' is formed as a roller bottle which is slowly rotated about a horizontal axis and contains a nutrient solution and cells to be grown. The container accumulates in the area 2. The container 1' has a cylindrical peripheral wall 7. The bristle-shaped projections extend inside the container from an inner surface of the cylindrical wall 7. During rotation of the container, successive parts of the inner surface of the cylindrical wall 7 and the respective bristle-shaped projections on them are supplied with the nutrient solution for growing cells. In this embodiment as well as in all other embodiments, the height of the bristle-shaped projections 5 is greater than their thickness.

Figure 7:
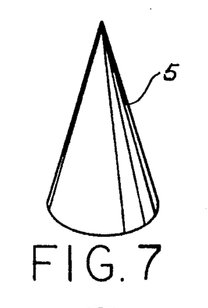
FIGS. 7–18 are schematic views showing bristle-shaped projections of the container for biological culture, having different shapes.
Figure 8:
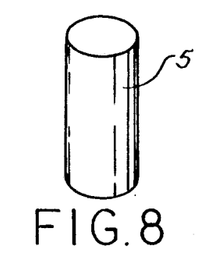
Figure 9:
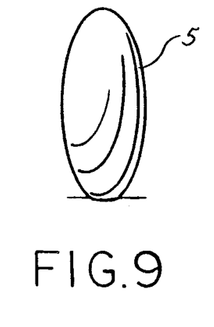
Figure 10:
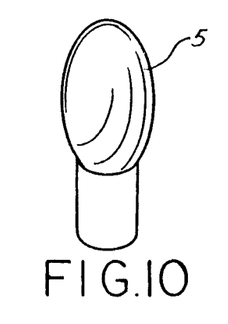
Figure 11:
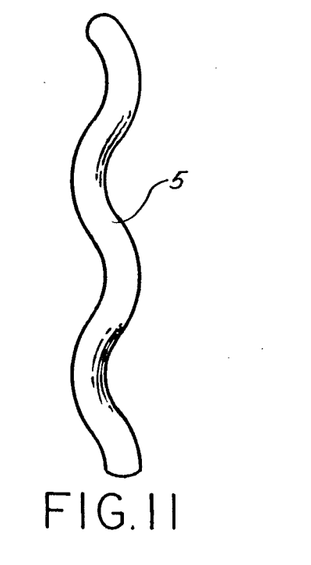
Figure 12:
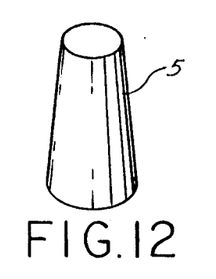
Figure 13:
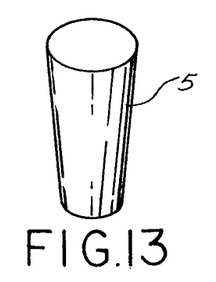
Figure 14:
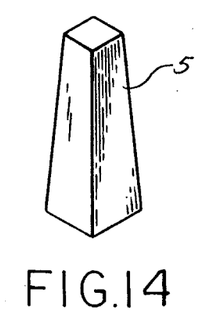
Figure 15:
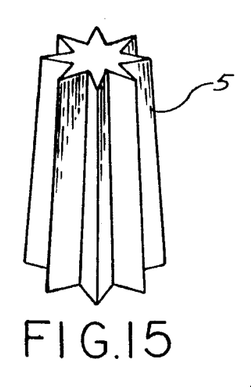
Figure 16:
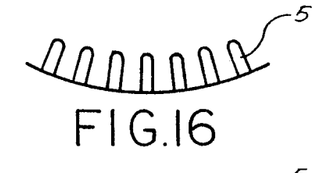
Figure 17:
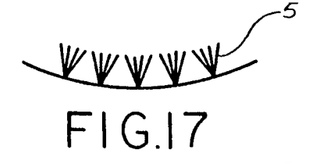
Figure 18:
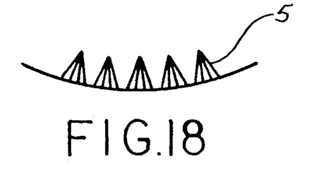

The bristle-shaped projections can have different shapes suitable for retaining and growing of the cells on them. FIG. 7 shows the bristle-shaped projection formed as a cone. FIG. 8 shows a bristle-shaped projection formed as a round cylinder. FIG. 9 shows a bristle-shaped projection formed as a vertically elongated globule. The bristle-shaped projection shown in FIG. 10 is mushroom-shaped. The bristle-shaped projection shown in FIG. 11 is vertically elongated and wave-shaped to further increase its useful surface. The bristle-shaped projections shown in FIGS. 12, 13 and 14 are formed as a truncated cone with a lower larger base, a truncated cone with an upper larger base, and a truncated pyramid respectively. FIG. 15 shows a bristle-shaped projection in form of a polyhydral pyramid with a lower greater base. FIG. 16 shows bristle-shaped projections formed as a plurality of loops. FIGS. 17 and 18 show bristle-shaped projections which are formed as bristles with apexes facing downwardly and upwardly, respectively.

Figures 19, 20, 21, 22, 23:
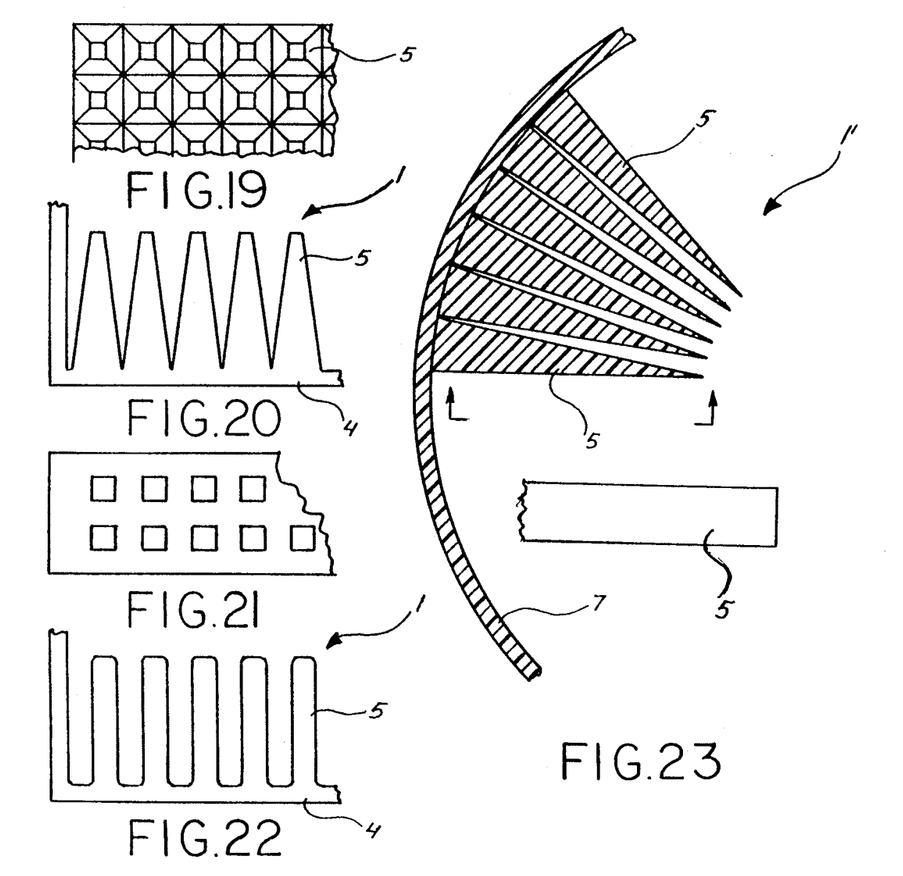
FIGS. 19, 20 and 21, 22 show a detailed plan view and a detailed side view of two further modifications of the bristle-shaped projections for a flask-type container for biological cultures.
FIGS. 23 and 24 are views showing two further modifications of the bristle-shaped projections for the container formed as a roller bottle.

FIGS. 19 and 20 show the bristle-shaped projections formed on the brush-shaped bottom of the container 1 and having the shape of pyramids. The flat tops of the pyramids are suitable for initial deposition of the cells, the bottoms of the pyramids merge into one another, and gaps are retained between the neighboring pyramids around each pyramid In the embodiment of FIGS. 21, 22 the bristle-shaped projections 5 extend upwardly from the brush-like bottom 4 and have an identical cross-section over their whole height. They are spaced from each other so that a free space is formed around each bristle-shaped projection.

The projection shown in FIGS. 19–22 are provided on the container 1 formed as a flask.

Figure 24:
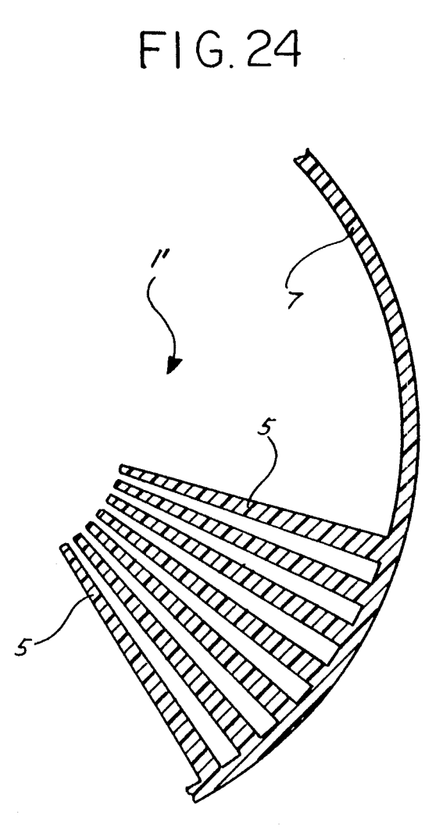

In the container shown in FIG. 23 and formed as a roller bottle 1', the bristle-shaped projections 5 extend from the cylindrical wall 7 toward the center of the container. At the cylindrical wall 7, they are in contact with one another and have their greater cross-section while their cross-section reduces toward the center of the container to form a pointed end. However, in a not shown section taken perpendicularly to the plane of the drawing, the cross-section of each bristle-shaped projection 5 does not reduce, but instead remains constant from its peripheral end to its central end. In the container 1' formed as a roller bottle and shown in FIG. 24, the bristle-shaped projections 5 also have a cross-section reducing from their peripheral end toward their central end in the plane of the drawings However, their central end is not pointed but instead has a certain thickness. In a section which is perpendicular to the plane of the drawings, the cross-section of the bristle-shaped projections 5 remain constant Thus, at the central end of each projection, a flat surface is formed.

It should be emphasized that the bristle-shaped projections 5 can be either rigid or flexible The rigidity or the flexibility of the projections can be achieved by selection of a rigid or a flexible material for the projections, by selection of the thickness of the projections, by selection of the shape of their cross-section, or by the attachment to the respective wall.

Figure 25:
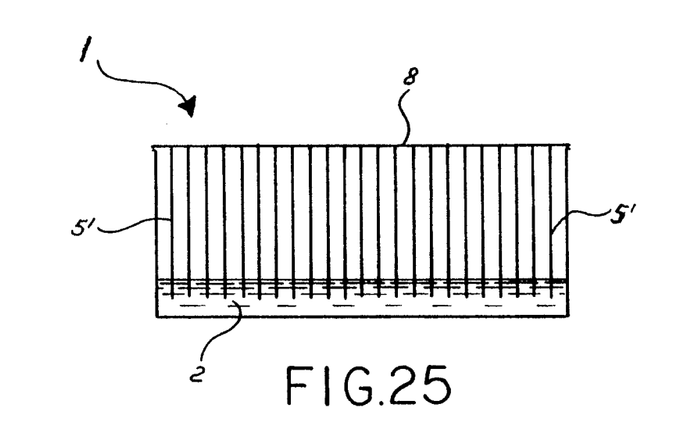
FIGS. 25–28 are schematic views showing a container formed as a flask in accordance with a further embodiment of the invention in four further modifications.
Figure 26:
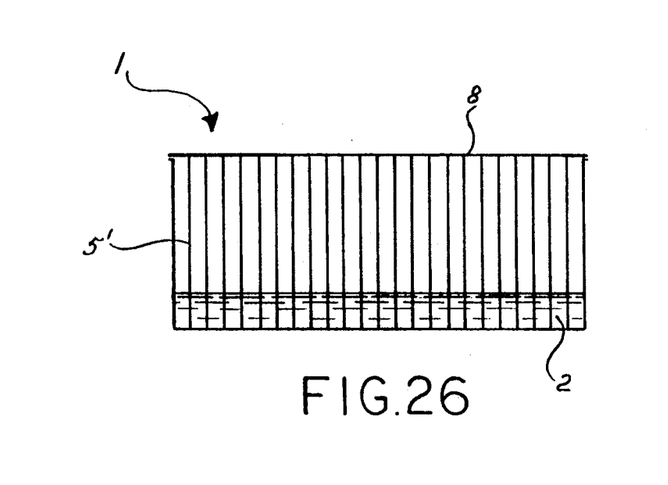
Figure 27:
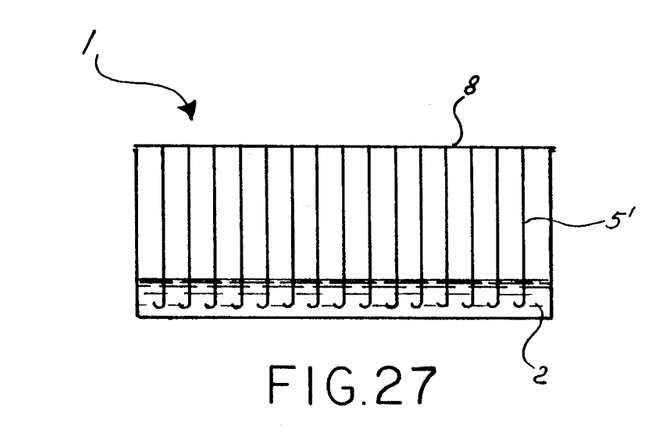
Figure 28:
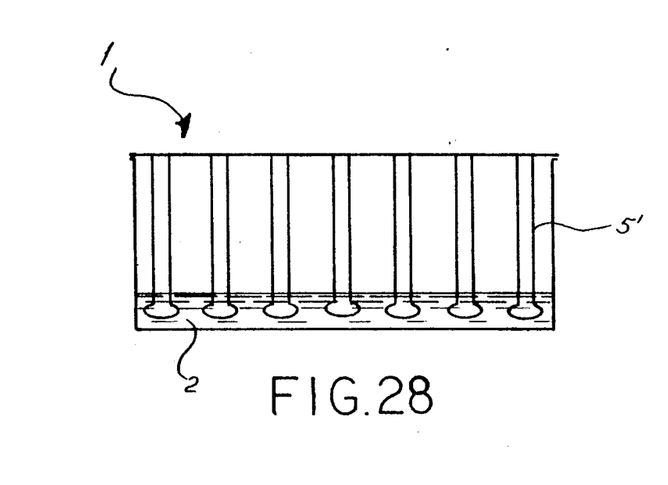
Figure 29:
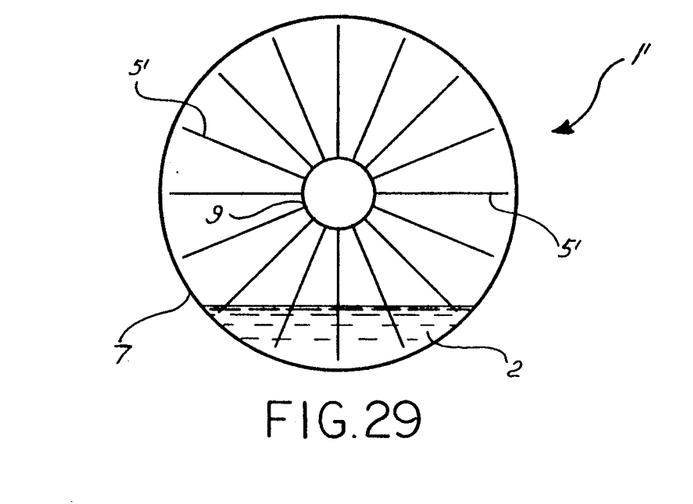
FIGS. 29–32 are end views showing a container formed as a roller bottle in accordance with a further embodiment with four further modifications.
Figure 30:
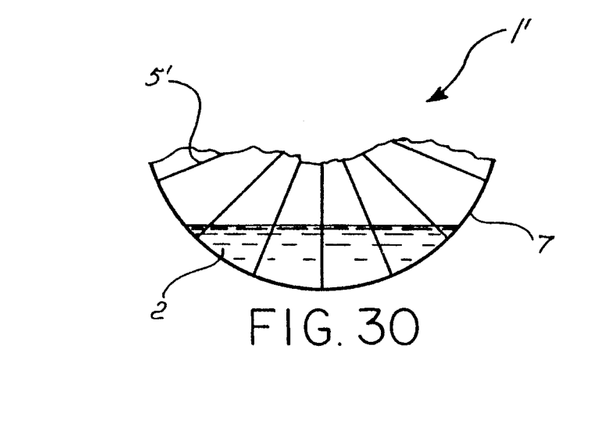
Figure 31:
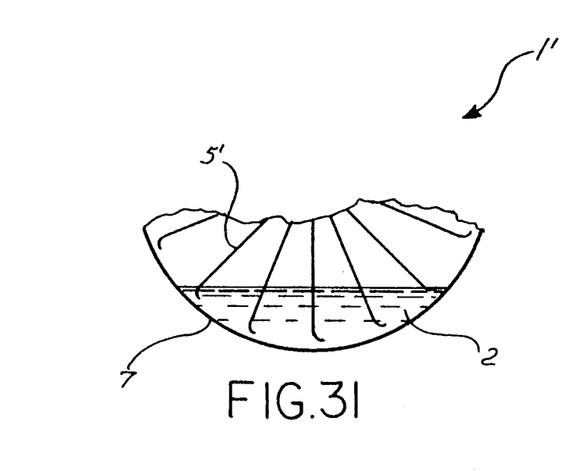
Figure 32:
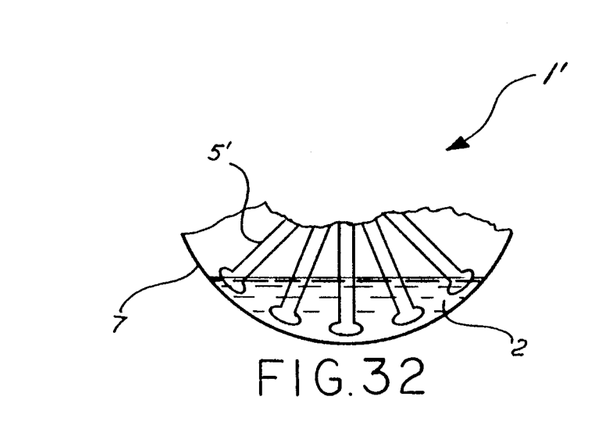

In the containers in accordance with the above described embodiments, the bristle-shaped projections are arranged so that they extend from the brush-like wall located near the area of accumulation of the nutrient solution and growing of cells. The containers in accordance with subsequent embodiments are formed differently from the containers of the above mentioned embodiments. The container 1 shown in FIG. 25 is formed as a flask which has the area 2 accumulating a nutrient solution and cells to be grown. The container 1 is provided with a plurality of bristle-shaped projections 5' which, contrary to the preceding embodiments, extend from a top 8 opposite to the bottom of the container. The bristle-shaped projections 5' extending downwardly to the area 2 so that they immerse in the nutrient solution. In the container shown in FIG. 25 the bristle-shaped projections 5' stop shortly before the bottom of the container, in the container shown in FIG. 26 the bristle-shaped projections 5' extend exactly to the bottom, in the embodiment shown in FIG. 27, the bristle-shaped projections 5' are curved in the region of the bottom and in the area 2, and in the container shown in FIG. 28 the bristle-shaped projections 5' have extended lower end portions in the area 2.

FIGS. 29–32 show the container 1' which is again formed as a roller bottle and in which the bristle-shaped projections 5' do not extend from the wall adjacent to the area 2 for accumulating a nutrient solution and growing cells, but instead extend from a different wall. More particularly, the bristle-shaped projections 5' extend from a central holder located in the center of the roller bottle. In the container shown in FIG. 29, the bristle-shaped projections 5' extend from the central holding 9 and stop shortly before the cylindrical wall 7 of the container, in the container shown in FIG. 30 the peripheral ends of the bristle-shaped projections 5' extend exactly up to the peripheral wall 7, in the container of FIG. 31 the bristle-shaped projections 5' are curved in the region of the peripheral wall 7 and in container shown in FIG. 32 the bristle-shaped projections have expanded end portions in the region of the peripheral wall 7.

Figure 33:
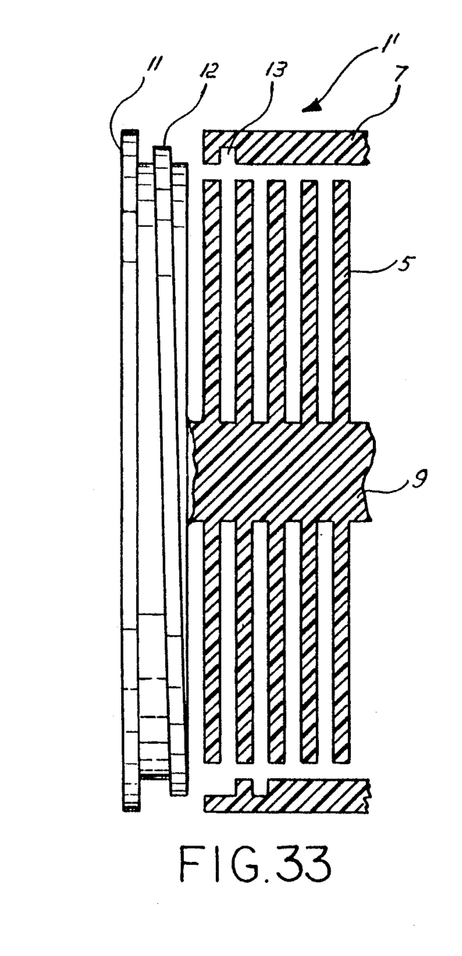
Figure 34:
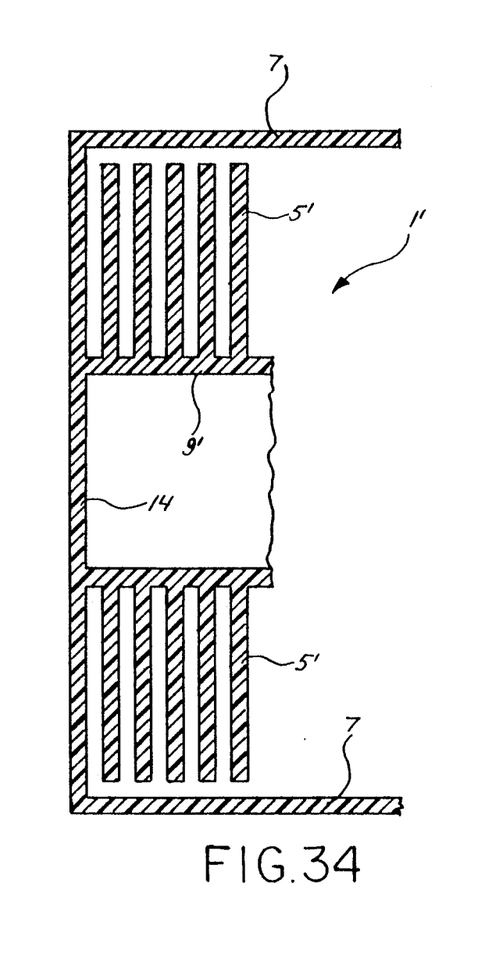
Figure 35:
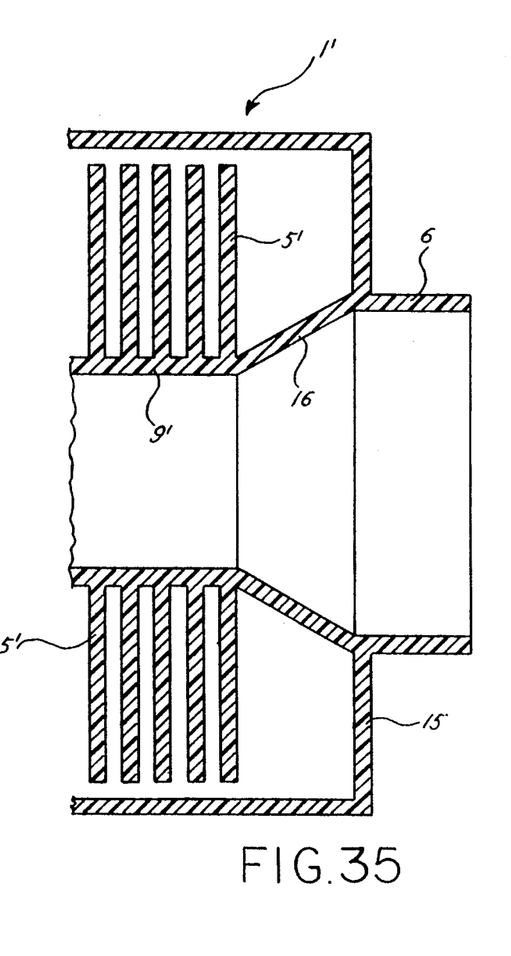

FIG. 33 shows how the central holder can be arranged in the container 1'. The central holder is mounted on an end plug 11 provided with a projection 12, while the peripheral wall 7 of the container is provided with a groove 13. The projection 12 is formed as a convolution of a screw. The bristle-shaped projections 5 are formed on the central holder 9. For introducing the bristle-shaped projections 5' into the inner chamber of the container 1', the assembly 5', 9, 11 is axially moved toward the container so that the projection 12 engages with the groove 13. The end opening of the container is firmly closed, and the bristle-shaped projections 5' are properly oriented in the interior of the container. In the container shown in FIG. 34 the central holder 9' is hollow and carries the bristle-shaped projections 5' on its outer periphery. The hollow holder 9' is formed of one piece with an end wall 14 of the container. In the container shown in FIG. 35, the bristle-shaped projections 5' are arranged on the hollow central support 9' which in turn is connected by an intermediate portion 16 with an end wall 15 of the container 1'. This arrangement can be formed in the region of the neck 6 of the container.

Figure 36:
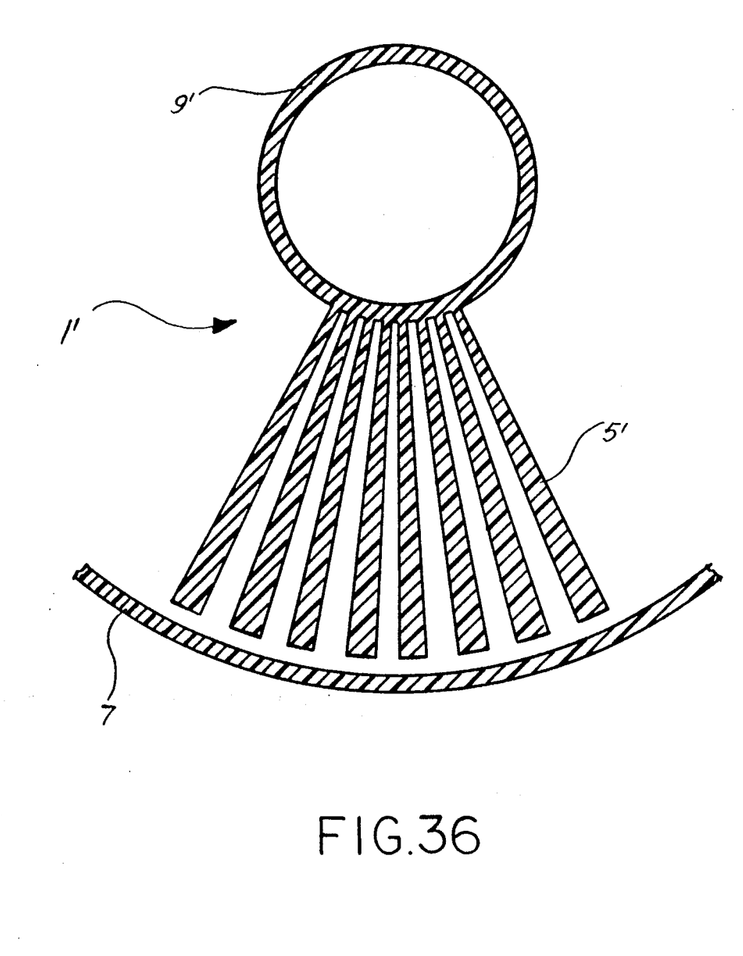
FIGS. 36, 37 are end views showing further modifications of an arrangement of bristle-shaped projections in the container formed as a roller bottle.
Figure 37:
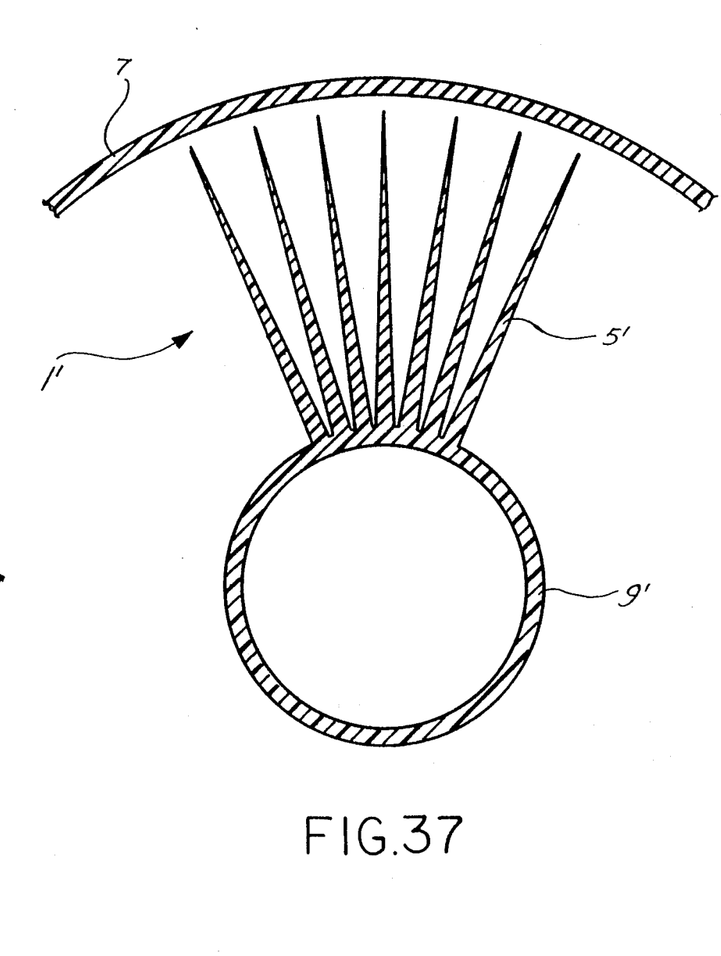

In the container 1' shown in FIG. 36, the bristle-shaped projections 5' extend from the central hollow holder 10' and have a cross-section which increases in direction from the center toward the periphery of the container. In contrast, in the container shown in FIG. 37, the projections 5' extending from the central holder 9' have a cross-section which increases in direction from the center towards the periphery of the container. The projections 5' shown in FIGS. 36 and 37 can have the same shape in the plane extending perpendicular to the plane of the drawings On the other hand, these projections in the plane perpendicular to the plane of the drawings, can have a shape which does not change in radial direction and remains the same from the central to the peripheral end.

It should be emphasized that when the container is formed with a bristle-shaped wall having a plurality of bristle-shaped sections extending into the area accumulating the nutrient solution and cells to be grown, the container has a drastically increased surface for growing cells and therefore provides for very high output.

What is claimed:

1. A container for a biological culture, particularly for growing cells, comprising a cylindrical wall limiting an inner chamber with an area for growing cells in a solution; a central holder located substantially in a center of said cylindrical wall; and a plurality of bristle-shaped projections extending from said central holder toward said cylindrical wall and into said area.

2. A container as defined in claim 1, wherein said bristle-shaped projections have a predetermined thickness and a height which is greater than said thickness.

3. A container as defined in claim 2, wherein the height of said bristle-shaped projections is many times greater than the thickness of said bristle-shaped projections.

4. A container as defined in claim 2, wherein the thickness of said bristle-shaped projections are several microns while the height of said bristle-shaped projections are several hundredth of a micron.

5. A container as defined in claim 1, wherein said bristle-shaped projections are substantially rigid.

6. A container as defined in claim 1, wherein said bristle-shaped projections are substantially flexible.

7. A container as defined in claim 1, wherein said bristle-shaped projections extend in a predetermined direction and have a cross-section which changes in said direction.

8. A container as defined in claim 1, wherein said bristle-shaped projections have a polyhydral shape with a side surface including a plurality of surfaces 9. A container as defined in claim 1, wherein said bristle-shaped projections are loop shaped.

10. A container as defined in claim 1, wherein said bristle-shaped projections are arranged in bundles.

11. A container as defined in claim 1, wherein said projections have a first end connected with said wall and an opposite free end having a flat surface.

12. A container as defined in claim 1, wherein said bristle-shaped projections have ends connected with said wall and arranged in contact with one another.

13. A container as defined in claim 1, wherein said bristle-shaped projections have ends connected with said wall and opposite free ends, said projections being spaced from one another at all sides of each projection from said first mentioned end to said free end.

14. A container as defined in claim 1, wherein said wall has an end wall portion connected with said central holder and engageable with the remaining portion of said wall.

15. A container as defined in claim 1, wherein said central holder which carries said bristle-shaped projections is formed as a hollow tubular holder.

16. A container as defined in claim 1, wherein said bristle-shaped projections have a thickness which vary along their length.

17. A container as defined in claim 16, wherein each of said bristle-shaped projections has a cross-section with two transverse dimensions, one of said dimensions varying along the length of the projection while the other of said dimensions remains constant.

18. A container as defined in claim 1, wherein said wall is cylindrical and has an inner surface, said bristle-shaped projections being arranged on said inner surface of said cylindrical wall and having the shape of a truncated pyramid.

* * * * *